US007030162B2

(12) United States Patent
Plachetka et al.

(10) Patent No.: US 7,030,162 B2
(45) Date of Patent: Apr. 18, 2006

(54) TREATMENT OF MIGRAINE HEADACHE

(75) Inventors: John R. Plachetka, Chapel Hill, NC (US); Zakauddin T. Chowhan, Gaithersburg, MD (US)

(73) Assignee: POZEN Inc., Chapel Hill, NC (US)

( * ) Notice: Subject to any disclaimer, the term of this patent is extended or adjusted under 35 U.S.C. 154(b) by 21 days.

(21) Appl. No.: 10/255,036

(22) Filed: Sep. 26, 2002

(65) Prior Publication Data

US 2003/0040537 A1    Feb. 27, 2003

Related U.S. Application Data

(60) Division of application No. 09/517,751, filed on Mar. 3, 2000, now Pat. No. 6,479,551, which is a continuation-in-part of application No. 08/966,506, filed on Nov. 10, 1997, now Pat. No. 6,077,539, which is a continuation-in-part of application No. 08/748,332, filed on Nov. 12, 1996, now abandoned.

(30) Foreign Application Priority Data

Nov. 12, 1997    (WO) .................... PCT/US97/20611

(51) Int. Cl.
*A61K 31/16*      (2006.01)
*A61K 9/00*       (2006.01)
*A61K 31/00*      (2006.01)
*A61P 25/06*      (2006.01)

(52) U.S. Cl. ................. 514/619; 424/451; 424/457; 424/458; 424/468; 424/472; 514/226.5; 514/277; 514/365; 514/374; 514/410; 514/411; 514/454; 514/568; 514/569; 514/570; 514/617; 514/646; 514/685; 514/686; 514/716; 514/717; 514/721; 514/727; 514/964

(58) Field of Classification Search ................ 514/406, 514/569, 570, 576, 577, 608, 619, 646, 709, 514/716, 717, 721, 964; 424/468, 470, 472, 424/473, 474, 475, 480, 482, 451, 457, 458
See application file for complete search history.

(56) References Cited

U.S. PATENT DOCUMENTS

| 2,099,402 | A | | 11/1937 | Keller ........................ 167/82 |
|---|---|---|---|---|
| 4,024,279 | A | | 5/1977 | Zor et al. ................... 424/319 |
| 4,235,971 | A | | 11/1980 | Howard et al. ............. 435/293 |
| 4,380,540 | A | | 4/1983 | Poyser et al. ............... 424/233 |
| 4,664,915 | A | | 5/1987 | Simonian ................... 424/128 |
| 4,999,226 | A | | 3/1991 | Schock et al. .............. 424/472 |
| 5,037,823 | A | | 8/1991 | Jones et al. .............. 514/222.8 |
| 5,055,306 | A | | 10/1991 | Barry et al. ................ 424/482 |
| 5,155,105 | A | | 10/1992 | Jones et al. .............. 514/223.5 |
| 5,288,507 | A | | 2/1994 | Sims et al. ................. 424/682 |
| 5,415,870 | A | | 5/1995 | Gergely et al. ............. 424/466 |
| 5,437,874 | A | * | 8/1995 | Bru et al. ................... 424/466 |
| 5,573,776 | A | | 11/1996 | Harrison et al. ............ 424/435 |
| 5,681,583 | A | | 10/1997 | Conte et al. ................ 424/472 |
| 5,885,616 | A | | 3/1999 | Hsiao et al. ................ 424/472 |
| 6,077,539 | A | * | 6/2000 | Plachetka et al. .......... 424/474 |
| 6,106,862 | A | | 8/2000 | Chen et al. ................. 424/468 |
| 6,479,551 | B1 | * | 11/2002 | Plachetka et al. .......... 514/619 |

FOREIGN PATENT DOCUMENTS

| BE | 881 967 | 6/1980 |
|---|---|---|
| CA | 1165242 | 4/1984 |
| CA | 2020018 | 6/1990 |
| EP | 0 774 253 | 5/1997 |
| EP | 0 823 255 A1 | 2/1998 |
| JP | 58-8020 | 1/1983 |
| WO | WO 95/22947 | 8/1995 |

OTHER PUBLICATIONS

STN/CAS online, file EMBASE, Acc. No. 1999161935, (Mandell, Cleveland Clinic Journal of Medicine (1999), 66/5, pp. 285-292), Abstract.*
Remington's Pharmaceutical Sciences (17th Ed. 1985), p. 1111.*
EP 0774253, abstract (1997).
BE 881967, abstract (1980).
STN/CAS online, file EMBASE, Acc. No. 1999161935 (Mandell, *Cleveland Clinic Journal of Medicine 66*:285-292 (1999), Abstract.
Albibi, et al., Metoclopramide: Pharmacology and Clinical Application, *Ann. Int. Med. 98*:86-95 (1983).
Andersson, et al., "Double-Blind Study of Naproxen vs. Placebo in the Treatment of Acute Migraine Attacks," *Cephalalgia 9*:29-32 (1989).
Bateman, et al., "Extrapyramidal Reactions to Metoclopramide and Prochlorperazine," *Quart J. Med. 71*: 307-311 (1989).
Baumel, Migraine: A Pharmacologic Review with Newer Options and Delivery Modalities, *Neurology 44*:S13-S17 (1994).
Becker, et al., "Pharmacokinetic Aspects of a Combination of Metoclopramide and Paracetamol. Results of a Human Kinetic Study and Consequences for Migraine Patients," *Arzneimittelforschung 42*:552-555 (1992) (including English Language Abstract).
Boureau, et al., "Comparison of Subcutaneous Sumatriptan with Usual Acute Treatments for Migraine," *Eur. Neurol. 35*:264-269 (1995).

(Continued)

*Primary Examiner*—John Pak
*Assistant Examiner*—Frank Choi
(74) *Attorney, Agent, or Firm*—Michael A. Sanzo; Fitch, Even, Tabin & Flannery (57) ABSTRACT

The invention is directed to pharmaceutical compositions useful in the treatment of migraine. The compositions contain metoclopramide and one or more NSAIDs in unit dosage form. By selecting NSAIDs that are non-acidic or segregating the metoclopramide and NSAID, the storage life of the compositions has been increased. Also disclosed are coordinated dosage forms for the sequential release of drugs. The invention encompasses methods of treating migraine using any of these dosage forms.

23 Claims, 5 Drawing Sheets

OTHER PUBLICATIONS

Capobianco, et al., "An Overview of the Diagnosis and Pharmacologic Treatment of Migraine," *Mayo Clin. Proc.* 71:1055-1066 (1996).

Chabriat, et al., "Combined Oral Lysine Acetylsalicylate and Metoclopramide in the Acute Treatment of Migraine: A Multicentre Double-Blind Placebo-Controlled Study," *Cephalalgia* 14:297-300 (1994).

Chabriat, et al., "Combined Aspirin amd Metoclopramide in the Acute Treatment of Migraine Attacks: A Review," *Headache Quarterly* 8:118-121 (1997).

Chrubasik, "Paracetamol and Metoclopramide in Fixed Combination," *Med. Montasschr. Pharm.* 19:110 (1996) (German Language).

Cohen, et al., "Migraine Headache and the Managed Care Formulary," *Drug Benefit Trends* 8:28-30,33-34,41 (1996).

Consumer Assoc., "Metoclopramide/Analgesic Combinations for Migraine," *Drug and Therapeutics Bulletin* 18:: 95-96 (1980).

Dechant, et al., "Sumatriptan: A Review of Its Pharmacodynamic and Pharmacokinetic Properties, and Therapeutic Efficacy in the Acute Treatment of Migraine and Cluster Headache," *Drugs* 43:776-798 (1992).

Diamond, et al., "Do Non-Steroidal Anti-Inflammatory Agents Have a Role in the Treatment of Migraine Headaches?," *Drugs* 37:755-760 (1989).

Edmeads, "Four Steps in Managing Migraine," *Postgraduage Medicine* 85:121-124, 127-128, 131, 132-134 (1989).

Eldor, et al., "Ergotamine-Metoclopramide for Migraine: Is It Enough?," *Cephalalgia* 32:466 (1992).

Ellis, et al., "The Efficacy of Metoclopramide in the Treatment of Migraine Headache," *Ann. Emerg. Med.* 22:191-195 (1993).

Gamst, "Oral Naproxen Formulations," *Scand. J. Gastroenterol.* 24:44-47 (1989).

Ganzini, et al., "The Prevalence of Metoclopramide-Induced Tardive Dyskinesia and Acute Extrapyramidal Movement Disorders," *Arch. Intern. Med.* 153:1469-1475 (1993).

Greiff, et al., "Pharmacokinetic Drug Interactions with Gastrointesinal Motility Modifying Agents," *Clin. Pharmacokinetics* 27:447-461 (1994).

Gupta, et al., "Effect of Metoclopramide on Gastric Ulceration and Secretion in Albino Rats," *Arch Int. Pharmacodyn.* 297:158-165 (1989).

Harrington, et al., "Metoclopramide: An Updated Review of Its Pharmacological Properties and Clinical Use," *Drugs* 25:451-494 (1983).

Hoemecke, et al., "Treatment of Migraine Attacks: Combination of Dihydroergotamine Tartrate and Paracetamol in Comparison with Individual Drugs and Placebo," *Med. Klin.* 88:642-648 (1993) (including English Language Abstract).

Hughes, "Metoclopramide in Migraine Treatment," *Med. J. Australia* 2:580 (1977).

Hugues, et al., "Repeated Doses of Combined Oral Lysine Acetylsalicylate and Metoclopramide in the Acute Treatment of Migraine," *Headache* 37:454-454 (1997).

Johnson, et al., "Naproxen Sodium in the Treatment of Migraine," *Cephalalgia* 5:5-10 (1985).

Kaa, et al., "Emergency Department Resource Use by Patients with Migraine and Asthma in a Health Maintenance Organization," *Ann. Pharmacotherapy* 29:251-256 (1995).

Kandler, et al., "Analgesic Action of Metoclopramide in Prosthetic Hip Surgery," *Acta. Anaesthesiol. Scand.* 37:49-53 (1993).

Kirby, et al., "Effect of Metoclopramide, Bethanechol, and Loperamide on Gastric Residence Time, Gastric Emptying, and Mouth-Cecum Transit Time," *Pharmacotherapy* 9:226-231 (1989).

Klapper, "Toward a Standard Drug Formulary for the Treatment of Headache," *Headache* 35:225-227 (1995).

Kumar, "Recent Advances in the Acute Management of Migraine and Cluster Headaches," *J. Gen. Intern. Med.* 9:339-348 (1994).

Manniche, et al., "The Pharmacokinetics of the Individual Constituents of an Aspirin-Metoclopramide Combination ('Migravess')," *Curr. Med. Res. Opin.* 9:153-156 (1984).

Mathew, "Serotonin $1_D$ ($5-HT_{1D}$) Agonists and Other Agents in Acute Migraine," *Advances in Headache* 15:61-81 (1997).

Mohnot, "Treatment of Intractable Headaches," *Neurology* 36:101 (1986).

Ottervanger, "Ketorolac for Severe Migraine," *Med. Sci. Bul.* 26:49 (1994).

Peroutka, "Beyond Monotherapy: Rational Polytherapy in Migraine," *Headache* 38:18-22 (1998).

Peroutka, "Dopamine and Migraine," *Neurology* 49:650-656 (1997).

Pfaffenrath, et al., "Analgesics and NSAIDs in the Treatment of the Acute Migraine Attack," *Cephalalgia* 15:14-20 (1995).

Pini, et al., "Disposition of Naproxen after Oral Administration During and Between Migraine Attacks," *Headache* 33:191-194 (1993).

Plosker, et al., "Sumatriptan: A Reappraisal of Its Pharmacology and Therapeutic Efficacy in the Acute Treatment of Migraine and Cluster Headache," *Drugs* 47:622-651 (1994).

Pradalier, et al., "Treatment Review: Non-Steroid Anti-Inflammatory Drugs in the Treatment and Long-Term Prevention of Migraine Attacks," *Headache* 28:550-557 (1988).

Pryse-Phillips, et al., "Guidelines for the Diagnosis and Management of Migraine in Clinical Practice," *Can. Med. Assoc. J.* 156:1273-1287 (1997).

Ross-Lee, et al., "Single-Dose Pharmacokinetics of Metoclopramide," *Eur. J. Clin. Pharmacol.* 20:465-471 (1981).

Ross-Lee, et al., "Aspirin Pharmacokinetics in Migraine. The Effect of Metoclopramide," *Eur. J. Clin. Pharmacol.* 24:777-785 (1983).

Saadah, et al., "Abortive Migraine Therapy with Oral Naproxen Sodium Plus Metoclopramide Plus Ergotamine Tartrate With Caffeine," *Headache* 32:95-97 (1992).

Scherl, et al., "Comparison of Dihydroergotamine with Metoclopramide Versus Meperidine with Promethazine in the Treatment of Acute Migraine," *Headache* 35:256-259 (1995).

Schwarzberg, "Application of Metoclopramide Specificity in Migraine Attacks Therapy," *Headache* 34:439-441 (1994).

Scott, "Dihydroergotamine: A Review of Its Use in the Treatment of Migraine and Other Headaches," *Clin. Neuropharmacology* 15:289-296 (1992).

Sevelius, et al., "Bioavailability of Naproxen Sodium and Its Relationship to Clinical Analgesic Effects," *Br. J. Clin. Pharmac.* 10:259-263 (1980).

Silberstein, "Migraine Symptoms: Results of a Survey of Self-Reported Migraineurs," *Headache* 35:387-396 (1995).

Tfelt-Hansen, et al., "The Effectiveness of Combined Oral Lysine Acetylsalicylate and Metoclopramide Compared with Oral Sumatriptan for Migraine," *Lancet* 346:923-926 (1995).

Tfelt-Hansen, et al., "Kombinationen af Oral Lysin-Acetylsalicylat og Metoclopramid Sammenlignet Med Oral Sumatriptan i Behandlingen af Migraeneanfald," *Videnskab og Praksis* 1586345-6349 (1996) (including English Language Abstract).

Tfelt-Hansen, et al., "Effervescent Metoclopramide and Aspirin (Migravess) Versus Effervescent Aspirin or Placebo for Migraine Attacks: A Double-Blind Study," *Cephalalgia* 4:107-111 (1984).

Thomson, "A Study to Compare Oral Sumatriptan with Oral Aspirin Plus Oral Metoclopramide in the Acute Treatment of Migraine," *Eur. Neurol.* 32:177-184 (1992).

Todd, et al., "Naproxen: A Reappraisal of Its Pharmacology, and Therapeutic Use in Rheumatic Diseases and Pain States," *Drugs* 40:91-137 (1990).

Tokola, et al., Effects of Migraine Attack and Metoclopramide on the Absorption of Tolfenamic Acid, *Br. J. Clin. Pharmac.* 17:67-75 (1984).

Tokola, et al., "Tolfenamic Acid, Metoclopramide, Caffeine and Their Combinations in the Treatment of Migraine Attacks," *Cephalalgia* 4:252-263 (1984).

Volans, "The Effect of Metoclopramide on the Absorption of Effervescent Aspirin in Migraine," *Br. J. Clin. Pharmac.* 2:57-63 (1975).

Von Seggern, et al., "Cost Considerations in Headache Treatment Part 2: Acute Migraine Treatment," *Headache* 36:493-502 (1996).

Welch, "Drug Therapy of Migraine," *New England J. Med.* 329:1476-1483 (1993).

Wilkinson, et al., "Migraine and Cluster Headache—Their Management with Sumatriptan: A Critical Review of the Current Clinical Experience," *Cephalalgia* 15:337-357 (1995).

Wright, et al., "Linearity of Metoclopramide Kinetics as Doses of 5-20 mg," *Br. J. Clin. Pharmac.* 26:469-473 (1988).

Internet Advertisement for Migraleve(1998).

Material Safety Data Sheet for Paracetamol D.C. (P.G.S.) (2001).

Abstract for *Powder Technology* 33:107-111 (1982), Krycer, et al., "The Role of Intra-Granular Porosity in Powder Compaction."

Abstract for *Drug. Dev. Ind. Pharm.* 26(8):885-889 (2000), Railkar, et al., "Evaluation and Comparison of a Moist Granulation Technique to Conventional Methods."

Abstract for *Drug Dev. Ind. Pharm.* 27(4):337-343 (2001), Railkar, et al., "Use of a Moist Granulation Technique (MGT) to Develop Controlled-Release Dosage Forms of Acetaminophen."

Day, et al., "Evaluation of an Enteric Coated Aspirin Preparation," *Aust. N.Z.J. Med.* 6:45-50 (1976).

Abstract of JP 58-8020 (1983).

Tfelt-Hansen, "A Double-Blind Study of Metoclopramide in the Treatment of Migraine Attacks," *J. Neurol. Neurosurg. Psychiatry* 43:396-371 (1980).

Moore, et al., "Drug Treatment of Migraine: Part 1. Acute Therapy and Drug-Rebound Headache," *Am. Family Physician* 56 (1997).

* cited by examiner

TREATMENT OF MIGRAINE HEADACHE

CROSS REFERENCE TO RELATED APPLICATION

This application is a division of U.S. Ser. No. 09/517,751, filed on Mar. 3, 2000 (now U.S. Pat. No. 6,479,551). Application Ser. No. 09/517,751 is a continuation-in-part of U.S. Ser. No. 08/966,506, filed on Nov. 10, 1997 (now U.S. Pat. No. 6,077,539), which is a continuation-in-part of U.S. Ser. No. 08/748,332, filed on Nov. 12, 1996 (now abandoned).

FIELD OF THE INVENTION

The present invention is directed to compositions comprising metoclopramide and a second drug, particularly an analgesic. These compositions may be used as a treatment for migraine and other disorders.

BACKGROUND

Migraine is a painful syndrome characterized by unilateral, pulsating headaches, nausea, vomiting, and sensitivity to light and sound. Approximately 23 million Americans presently suffer from this disorder. Drugs that have been used in an attempt to treat migraine include: ergotamine and ergotamine-like agents; serotonin agonists; and caffeine with ergots or other pharmacologic agents (see e.g., Silberstein, S. D., Curr. Opinion Neurology 7:258–263 (1994); Welch, K. M. A., New Engl J. Med. 329:1476–1483 (1993); Kumar, K. L., J. Gen. Int. Med. 9:339–348 (1994); Saadah, H., Headache 32:95–97 (1992); and Becker, Arzneimittelforshung 42(4):552–555 (1992)). All of these drugs are thought to initially relieve migraine-associated pain by causing vasoconstriction. Unfortunately, this leads to numerous side effects such as chest pain or pressure, flushing, generalized tingling sensations, nausea, vomiting, pain in the legs and arms, asthenia, drowsiness, and dizziness. Acute ergotism is a particularly pernicious side effect of ergot drugs and is characterized by severe central and peripheral vasoconstriction, nausea, vomiting, diarrhea, colic, headache, vertigo, paresthesia, and possibly convulsive seizures.

Patients have, on occasion, found total or partial relief for some forms of migraine through the use of non-prescription analgesics. As outlined by Welch (New Engl J. Med. 329: 1476–1483 (1993)), the initial dosages of such analgesics are typically: aspirin, 500–650 mg; acetaminophen, 500 mg; naproxen sodium, 750–825 mg; tolfenamic acid, 200–400 mg; and, ibuprofen 200 mg. After oral dosing, peak plasma concentrations in normal subjects usually occur at about 1 hour for aspirin and acetaminophen, and between 1 and 2 hours for naproxen sodium, tolfenamic acid, and ibuprofen. However, the absorption of these and other agents during a migraine attack has been shown to be impaired, apparently due to gastric stasis.

Ideally a migraine drug formulation should be nonaddictive and free of vasoactive agents (i.e. agents causing the constriction or dilation of blood vessels). This requires the exclusion of ergots, serotonin agonists such as sumatriptan (including related 5HT agonist heterocyclic compounds as described in U.S. Pat. No. 4,816,470) and caffeine. The formulation should relieve pain, reduce gastric stasis, reduce nausea, and allow for a faster rate of drug absorption.

Metoclopramide is a drug known to relieve migraine-associated nausea when administered at a minimum oral dose of 10 mg. Poyser et al. have described a formulation in which aspirin is uniformly intermixed with metoclopramide (U.S. Pat. No. 4,380,540). One drawback of this formulation is that it undergoes unacceptable degradation in a matter of two to three weeks at ambient temperatures. In addition, aspirin is known to have a very short plasma half life. New formulations of metoclopramide that are effective in treating migraine headache and that avoid the disadvantages of this and other previously disclosed preparations would represent a clear advance in the art.

SUMMARY OF THE INVENTION

The present invention is based upon the discovery of improved formulations for the treatment of migraine headache. The formulations contain a combination of metoclopramide and one or more analgesics (preferably NSAIDs) and are prepared in such a manner as to avoid the loss of activity that has been observed to sometimes accompany such formulations. In particular, it has been discovered that loss of activity occurs when an acidic analgesic is in prolonged contact with metoclopramide. Thus, compositions that utilize non-acidic analgesics (i.e., analgesics having a $pK_a$ of 7 or above when dissolved in water) or in which metoclopramide and analgesic are separated offer substantial advantages. In addition, new dosage forms have been developed that have improved therapeutic characteristics. Specifically, improved absorption of drug has been accomplished using "coordinated" dosage forms in which metoclopramide and NSAID are sequentially delivered. Improved characteristics may also be obtained by using long-acting analgesics or analgesics that are formulated to be long acting.

In its first aspect, the present invention is directed to a pharmaceutical composition in unit dosage form suitable for oral administration in the treatment of migraine headache. The dosage form contains metoclopramide in an amount effective to increase gastric motility in a patient suffering from a migraine attack and a non-acidic analgesic (preferably a non-acidic NSAID) in an amount effective to reduce or eliminate headache pain. Preferably, the dosage form should be either a tablet or capsule and should be free from vasoactive agents, including 5 HT agonist vasoactive agents. The dosage form may be coordinated for the sequential delivery of drugs and may incorporate long-acting NSAIDs, including cyclooxygenase-2 inhibitors. Alternatively, the dosage form may contain analgesics formulated to be long acting. The most preferred non-acidic NSAID is Celecoxib (Celebrex®), typically in an amount of between 25 and 250 mg. It is desirable that sufficient metoclopramide be present to reduce or eliminate the nausea associated with migraine headache. Typically, a dosage form will have between 1 mg and 100 mg of metoclopramide.

In a second aspect, the invention is directed to a pharmaceutical composition in unit dosage form that has been acid-base storage stabilized. Metoclopramide and one or more analgesics (preferably NSAIDs) are present in an amount such that their combination is effective in reducing or eliminating headache pain. Acid-base storage stabilization is accomplished by constructing dosage forms in a manner that eliminates or minimizes contact between the drugs during storage. For example, tablets or capsules may be made in which either metoclopramide or analgesic is barrier coated. Alternatively, metoclopramide and analgesic may be in separate layers of a multilayer tablet. Dosage forms should typically be free of vasoactive agents, may be coordinated and may contain either long-acting NSAIDs or NSAIDs formulated to be long acting. Typical NSAIDs that may be used include: acetaminophen; ibuprofen; flurbiprofen; ketoprofen; naproxen; oxaprozin; etodolac; indomethacin; ketorolac; nabumetane; piroxicam; celecoxib; rofecoxib; meloxicam; JTE-522; L-745,337; NS398; and pharmaceutically acceptable salts thereof. The most preferred analgesic is naproxen. This should be present at between 50 mg and 1500 mg and preferably at between 200 and 600 mg. Although any form of naproxen is compatible with the invention, naproxen sodium is generally preferred.

More generally, the present invention encompasses pharmaceutical compositions in unit dosage form that contain at least one analgesic (preferably an NSAID) in combination with metoclopramide and which are either coordinated or in which at least one analgesic is long acting or formulated to be long acting. In all cases, the combination of drugs should be effective to reduce or eliminate headache pain. Long acting NSAIDs suitable for use in the dosage forms include: ibuprofen; flurbiprofen; ketoprofen; oxaprozin; etodolac; indomethacin; ketorolac; nabumetane; piroxicam; celecoxib; rofecoxib; meloxicam; JTE-522; L-745,337; NS398; or pharmaceutically acceptable salts thereof. When naproxen, the preferred analgesic, is used, it should be present in an amount of between 50 and 1500 mg and preferably between 200 and 600 mg. The sodium salt of naproxen is generally preferred. Analgesics that may be formulated to be long acting include ibuprofen, aspirin and acetaminophen. Methods for making appropriate long acting formulations for these and other analgesics are well known in the art (see, e.g., *Remington's Pharmaceutical Sciences*, 16th ed., A. Oslo editor, Easton Pa. (1980); *Controlled Drug Delivery*, 2nd rev. and ex. ed., Joseph R. Robinson & Vincent H. L. Lee eds., Marcel Dekker (1987), ISBN: 0824775880; *Encyclopedia of Controlled Drug Delivery*, Edith Mathiowitz, John Wiley & Sons (1999), ISBN: 0471148288). Coordinated dosage forms should be suitable for oral delivery and will typically take the form of a tablet or capsule. Metoclopramide and NSAID may be in separate layers of a multilayer tablet and, in general, these dosage forms should be substantially free of vasoactive agents such a 5 HT agonists.

Pharmaceutical compositions containing analgesics (e.g., long-acting NSAIDs or NSAIDs formulated to be long acting) may be acid-base storage stabilized or coordinated and should, preferably, be suitable for oral administration (e.g. in the form of a tablet of capsule). It will also generally be advantageous for metoclopramide to be present at a concentration effective to reduce or eliminate the nausea associated with migraine headaches.

The present invention is also directed to methods of treating patients for migraine headaches. This may be accomplished by administering an amount of any of the dosage forms described above effective to reduce or eliminate one or more of the symptoms associated with a migraine attack. More generally, patients may be administered metoclopramide in conjunction with an analgesic. A sufficient amount of these drugs should be given so that, in combination, they reduce or eliminate headache. Preferably, patients should not be administered vasoactive agents such as 5 HT agonists. Long-acting analgesics and analgesics formulated to be long acting may be used in the method. NSAIDS that can be used include: acetaminophen (when formulated to be long acting); ibuprofen; flurbiprofen; ketoprofen; naproxen; oxaprozin; etodolac; indomethacin; ketorolac; nabumetane; piroxicam; celecoxib; rofecoxib; meloxicam; JTE-522; L-745,337; NS398; orpharmaceutically acceptable salts thereof. In general, naproxen is the most preferred NSAID, particularly when in the form of naproxen sodium.

In addition, the invention encompasses methods of increasing the rate of absorption of a drug into the bloodstream of a patient by administering it together with metoclopramide in a coordinated dosage form. As described above, the metoclopramide should be released first in an amount effective to increase gastric motility. A therapeutically effective amount of the drug should then be released and reach the gastrointestinal tract of the patient during the period that metoclopramide is having its effect. For the purposes of this invention absorption is defined as the time from which the drug is administered until the time that it reaches a peak plasma concentration. This treatment will be particularly effective in patients suffering from conditions associated with gastric stasis. For example, as suggested from the above discussion, migraine patients may be administered analgesics. Typically, analgesics will be administered, with long-acting NSAIDs and particularly naproxen being preferred.

DETAILED DESCRIPTION OF THE INVENTION

The present invention is based upon the discovery of several improved pharmaceutical compositions for administering analgesics, particularly NSAIDs, to migraine patients. The first of these involves a unit dosage form that has metoclopramide and a non-acidic analgesic. The metoclopramide should be present in an amount of between 1 and 100 mg and preferably between 2 and 20 mg. It should also be "rapidly available," i.e. sustained release formulations of metoclopramide will be generally undesirable. The formulation should typically be free of vasoactive agents to avoid side effects and the analgesic used should be non-acidic to avoid the loss of activity that has been found to result from prolonged contact between metoclopramide and acidic drugs, e.g. aspirin.

The effectiveness of a dosage form containing metoclopramide and an acidic analgesic may be maintained if the drugs do not have substantial direct contact with one another. For example, either metoclopramide or an NSAID may be coated with material that serves as a barrier to prevent interaction or the drugs may be segregated into different layers of a multilayer tablet. Methods for producing "acid-base storage stabilized" dosage forms are described in the Examples section below. Such dosage forms may, of course, be used with non-acidic analgesics as well and, preferably, are devoid of vasoactive agents. The preferred analgesic is naproxen at between 200 and 600 mg.

A dosage form may also provide for coordinated delivery, i.e., delivery in which there is the sequential release of metoclopramide followed by analgesic. Again, methods for producing this type of dosage form are described below. Coordinated dosage forms in which metoclopramide is used to promote drug absorption from the GI tract may also be used to administer agents other than analgesics and will be particularly useful for treating diseases or conditions associated with gastric stasis.

Because migraine attacks are often prolonged, dosage forms having long acting analgesics, preferably, long acting NSAIDS, are greatly preferred. For example, naproxen (with a half life of 12–15 hours) and oxaprozin (with a half-life of about 42 to 50 hours) are particularly well suited for the treatment of migraine patients. Alternatively, analgesics may be specially formulated to be long acting.

Features of the dosage forms described above may, if desired be combined. For example, an acid-base stabilized dosage form may also be coordinated and contain a long acting NSAID. In all cases, it is preferred that formulations for the treatment of patients be free from vasoactive agents and that they be suitable for oral administration.

Making of Pharmaceutical Preparations

The pharmacologically active compositions of the invention can be made in accordance with methods that are standard in the art (see, e.g., *Remington's Pharmaceutical Sciences,* 16th ed., A. Oslo editor, Easton Pa. (1980)). Drugs and drug combinations will typically be prepared in admixture with conventional excipients. Suitable carriers include, but are not limited to: water; salt solutions; alcohols; gum Arabic; vegetable oils; benzyl alcohols; polyethylene glycols; gelatin; carbohydrates such as lactose, amylose or starch; magnesium stearate; talc; silicic acid; viscous paraffin; perfume oil; fatty acid esters; hydroxymethylcellulose; polyvinyl pyrrolidone, etc. The pharmaceutical preparations can be sterilized and, if desired, mixed with auxiliary agents, such as: lubricants; preservatives; stabilizers; wetting agents; emulsifiers; salts for influencing osmotic pressure; buffers; coloring agents; flavoring agents; and/or aromatic substances.

For non-parenteral applications, particularly suitable dosage forms are tablets, dragees, liquids, drops, suppositories, and capsules. Sublingual and buccal forms may also be used. Sustained or directed release compositions can be formulated, in which the active components are protected with differentially degradable coatings, e.g., by microencapsulation, multiple coatings, etc. It is also possible to freeze-dry compositions and use the lyophilizates for the preparation of products for injection.

Generally, the compositions of this invention will be dispensed in a unit dosage form comprising about 2–30 mg of metoclopramide and about 200–1000 mg of naproxen sodium or equivalent doses of other NSAIDs in a pharmaceutically acceptable carrier. Dosages for a given patient can be determined using methods well known in the art.

The Making of Tablet Dosage Forms

The combination of metoclopramide and an analgesic may take place in a single layer tablet or other solid dosage form. A bi- or multi layer tablet of the type described in this invention relieves nausea, improves gastrointestinal motility which enhances the speed of absorption of the NSAID, and provides an enhanced therapeutic effect against migraine symptoms in patients.

In a bilayer configuration, one portion of the tablet contains metoclopramide in the required dose and appropriate excipients, agents to aid dissolution, lubricants, fillers, etc., and is, preferably, designed to dissolve to 90% completion in the stomach in less than about 10 minutes, thus increasing gastrointestinal motility and controlling nausea. The effect of the rapid availability of metoclopramide is to accelerate delivery of the naproxen (or other analgesic) to the small intestine which is the site of most rapid absorption. In a bilayer tablet embodiment, the second portion of the tablet will contain, preferably, naproxen sodium in the required dose and appropriate excipients, agents to aid dissolution, lubricants, fillers, etc. It should generally dissolve up to 90% completion after the metoclopramide portion has dissolved and within about 60 minutes.

In one embodiment of bilayer tablet preparation, once the two components have been manufactured, they are combined into a single tablet. This process allows for different dosages of either component (i.e. the metoclopramide component or the naproxen sodium component) to be usefully combined into a single tablet in an efficient way. In another embodiment, substantially each naproxen sodium crystal (or metoclopramide particle) is coated with a rapid dissolving excipient material, conveniently, prior to tableting.

Powder flow characteristics and powder compressibility are the main criteria to be considered with respect to successful tablet production. To improve compressibility, naproxen sodium may be granulated. This involves increasing granule size through the addition of excipients that provide binding properties as well as disintegration properties. Granulation methods can be performed in a dry or wet state and include: "slugging;" low- or high-shear granulation; wet granulation; and, fluidized-bed granulation. Of these processes, slugging generally produces tablets of less hardness and greater friability. Low-shear granulation, high-shear granulation, wet granulation and fluidized-bed granulation generally produce harder, less breakable tablets.

Useful dosages of other analgesics to combine with metoclopramide include aspirin (particularly about 325–1000 mg and 500–650 mg), phenacetin, and acetaminophen (particularly about 325–1000 mg). Such analgesics may be formulated to be long acting or may be in a coordinated dosage form. In cases where the analgesic is acidic (e.g. aspirin), acid base stabilized dosage forms should be used, e.g., the acidic analgesic and the metoclopramide may be sequestered to different layers of a multilayer tablet in such a manner that contact between the drugs is eliminated or minimized. In the case of COX-2 inhibitors, the non-acidic analgesic Celecoxib (Celebrex®) is particularly useful when contained in tablets of from about 100 to 200 mg. Celecoxib peak plasma concentrations occur approximately 3 hours after oral dosing. The effective half-life is approximately 11 hours.

Definitions

A. "Long acting" in relation to NSAIDs and other analgesics shall mean a pharmacokinetic half-life of at least about 2 hours and preferably 8–14 hours. Particular preferred analgesics are flurbiprofen with a half-life of about 6 hours; ketoprofen with a half-life of about 2 to 4 hours; naproxen ((+(s)-6-methoxy-α-methyl-2-naphthaleneacetic acid) and naproxen sodium with half-lives of about 12 to 15 hours and about 12 to 13 hours respectively; oxaprozin with a half-life of about 42 to 50 hours; etodolac with a half-life of about 7 hours; indomethacin with a half-life of about 4 to 6 hours; ketorolac with a half-life of up to about 8–9 hours; nabumetane with a half-life of about 22 to 30 hours; mefenamic acid with a half-life of up to about 4 hours; and piroxicam with a half-life of about 4 to 6 hours. If an analgesic does not naturally have a half life sufficient to be long acting, it can be made long acting by the way in which it is formulated.

B. "Therapeutically effective amount" shall mean the dosage of drug that provides the specific pharmacological response for which the drug is administered in a significant number of subjects in need of such treatment. It is emphasized that migraine headache is not well understood and the etiology of particular migraines vary, as does the response to particular drugs. Thus reference to "specific pharmacological response for which the drug is administered in a significant number of subjects in need of such treatment" is a recognition that a "therapeutically effective amount," administered to a particular subject in a particular instance will not always abort a migraine attack or relieve an actual migraine headache, even though such dosage is deemed "therapeutically effective" by those skilled in the art. It is to be further understood that drug dosages are, in particular instances, measured as oral dosages, or parenteral or inhaled dosages or with reference to drug levels as measured in blood.

Metoclopramide hydrochloride monohydrate is conveniently provided in conventional tablets of 5 and 10 mg, as a solution of 5 mg/5 ml and as an injectable solution of 5 mg/ml. Although metoclopramide is not recognized by the FDA as an effective agent for the treatment of migraine, practitioners find doses of at least 10 mg by injection i.m. or intravenously to be useful for the treatment of the nausea accompanying migraine. Oral doses of 10–20 mg are less useful because it takes longer for therapeutic blood levels to be reached, resulting in a slower onset of action.

Dosages of analgesics will be adjusted by physicians based upon clinical factors. Nevertheless, some generalizations can be made. Indomethacin should be useful when present in tablets in a range of from about 25 to 75 mg, when present in suppositories at about 50 mg, and when in oral suspensions at a concentration of about 25 mg/5 ml. A typical daily oral dosage of indomethacin is three 25 mg doses taken at intervals during one day. However, daily doses of up to about 150 mg are also useful in some subjects. Sustained release dosage forms of indomethacin are also available and provide longer lasting blood levels than conventional tablets. In particular, a 25 mg sustained release dosage form can be used as an alternative to 25 mg three times daily or 75 mg twice daily can be substituted for 50 mg three times daily.

Ibuprofen is conveniently provided in tablets or caplets of 50, 100, 200, 300, 400, 600, and 800 mg and as a suspension of 100 mg/5 ml. Daily doses should not exceed 3200 mg and doses should be individualized. 200 mg–800 mg may be particularly useful when given 3 or 4 times daily.

Flurbiprofen is useful when in tablets at about 50 to 100 mg. Daily doses of about 100 to 500 mg, and particularly about 200 to 300 mg total are usually effective.

Ketoprofen is particularly useful when contained in capsules in an amount of about 25 to 75 mg. Daily doses of about 100 to 500 mg, and particularly about 100 to 300 mg are useful, as is about 25 to 50 mg every six to eight hours.

Naproxen is particularly useful when contained in tablets of from 250 to 500 mg, and in oral suspensions of about 125 mg/5 ml. For naproxen sodium, tablets of about 275 or about 550 mg are particularly useful. Initial doses of about 100 to 1250 mg, and particularly 350 to 800 mg, are also useful with doses of about 550 mg being generally preferred.

Oxaprozin is notable for having a pharmacokinetics half-life of 42–50 hours and a bioavailability of 95%. It is usefully provided as caplets of 600 mg. Daily doses of 1200 mg have been found to be particularly useful and daily doses should not exceed 1800 mg or 26 mg/kg. The lowest effective dose should always be used.

Etodolac is usefully provided in capsules of 200 mg and 300 mg and in tablets of 400 mg. Useful doses for acute pain are 200–400 mg every 6–8 hours, not to exceed 1200 mg/day. Patients weighing less than 60 kg are advised not to exceed doses of 20 mg/kg. Doses for other uses are also limited to 1200 mg per day in divided doses, particularly 2, 3, or 4 times daily.

Ketorolac is usefully provided in tablets of 10 mg and as a sterile parenteral preparation for injection in 15 mg/ml and 30 mg/ml dosage forms. Oral doses of up to 40 mg, and particularly 10–30 mg per day and parenteral doses up to 120–150 mg per day have been useful in the amelioration of pain.

Nabumetane may be provided in tablets of between 500 mg and 750 mg. Daily doses of 1500–2000 mg/day after an initial dose of 1000 mg are of particular use.

Mefenamic acid is particularly useful when contained in capsules of about 250 mg. For acute pain such as migraine, an initial dosage of 1 to 1000 mg and particularly about 500 mg is useful, though other dosages may be required for specific subjects.

Meclofenamate sodium is provided as capsules of 50 mg and 100 mg. Daily doses of up to 400 mg may be used. Typically a patient will take 50–100 mg every 4–6 hours.

One particular group of long acting NSAIDs that may be used are the cyclooxygenase-2 ("COX-2") inhibitors, for example: celecoxib, rofecoxib, meloxicam, piroxicam, JTE-522, L-745,337, or NS398, or pharmaceutically acceptable salts thereof. JTE-522, L-745,337 and NS398 are described, inter alia, in Wakitani, et al., *Jpn. J. Pharmacol.* 78:365–371 (1998); and Panara, et al., *Br. J. Pharmacol.* 116:2429–2434 (1995). The amount present in a tablet or administered to a patient will depend upon the particular COX-2 inhibitor being used. For example, piroxicam may be present at 10 to 20 mg per tablet. Celecoxib may be administered to a human in an amount of from about 100 mg to about 500 mg or preferably, in an amount of from about 100mg to about 200mg.

D. "Effective local gastrointestinal concentration" shall be understood to mean a dosage of metoclopramide that produces local improvement in gastric motility, with particular reference to the pyloric sphincter in subjects undergoing a migraine attack. While displaying variance from subject to subject, effective local gastrointestinal concentrations exhibit a peak blood level of from about 1 to about 150 ng/ml in 20 minutes.

E. "Co-timely" as to metoclopramide/analgesic combination drug therapy shall mean administration of an analgesic while metoclopramide is present or becomes present, in an effective local gastrointestinal concentration. In a preferred embodiment of co-timely drug administration, both drugs are administered in a single oral unit dosage form.

F. "Coordinated" in the practice of the present invention refers to the sequential administration of metoclopramide and at least one drug, preferably an NSAID, wherein the metoclopramide is available in an effective concentration at the gastrointestinal tract of the subject within 1 to 30 minutes after administration (preferably in 5 minutes or less and, more preferably, in 3 minutes or less). At least one analgesic should be initially available at a therapeutically effective level in 5 to 60 minutes after administration. The therapeutically effective level of the analgesic should not be attained until after metoclopramide is present at an effective local gastrointestinal concentration.

To establish the sequential dissolution of dosage forms, standard USP dissolution methods and apparatus are useful. In humans, the peak blood levels of naproxen sodium produced by the invention often occur at least 15–30 minutes more quickly than with standard USP tablets of naproxen sodium. Furthermore, migraine symptom relief will occur statistically more quickly and more often than with standard USP tablets of naproxen sodium.

The time to peak plasma levels for particular NSAIDs is as follows: flurbiprofen peaks in about 1 to 2 hours; ketoprofen peaks in about one-half to 2 hours; naproxen and naproxen sodium peak at about 2 to 4 hours and 1 to 2 hours respectively; oxaprozin peaks at about 3 to 5 hours; etodolac peaks at about 1 to 2 hours; indomethacin peaks at about 1 to 4 hours; ketorolac peaks at about one-half to 1 hour; nabumetane peaks at about 2.5 to 4 hours; mefenamic peaks at about 2 to 4 hours; meclofenamate peaks in 0.5–1 hours; and piroxicam peaks at about 3 to 5 hours.

G. "Rapid availability" as to metoclopramide in an oral dosage form shall be understood to be essentially the complete solubilization of metoclopramide from the dosage form within 30 minutes and preferably within 5 minutes from ingestion. Clearly, an oral dosage form of metoclopramide which is liquid at the time of administration would also represent a "rapid availability" form.

H. "Non-vasoactive" shall mean the substantial absence of demonstrated direct activity (either dilation or constriction) at therapeutic doses on either local or systemic arterial or venous blood vessels. Migraine attacks are associated with dilation of blood vessels in the head, and relief of a migraine headache has been associated with a reduction of such vasodilation.

I. "5HT agonist vasoactive agents" refers to a class of 5HT agonists with selective or non-selective vasoactivity on blood vessels including sumatriptan and all compounds either structurally and/or pharmacologically similar to it, ergotamine and all compounds either structurally and/or pharmacologically similar to it, and other serotonin agonists that exert a vasoactive effect. Metoclopramide, while having minimal 5HT agonist activity is excluded from the definition of 5HT vasoactive agents because of its insignificant activity on blood vessels at therapeutic doses.

"Ergots" refers to derivatives of 6-methylergoline. This includes forms with a substituent in the β configuration at position 8 and a double bond in ring D. Particular note is made of the amide derivatives of d-lysergic acid, a group of compounds which contain a double bond between C9 and C10. Many pharmaceutically active members of this class contain a methyl or hydroxymethyl group at position number 8, and are termed clavine alkaloids. Additional note is made of ergocornine, ergocristine, α-ergocryptine and β-ergocryptine, and ergonovine. Synthetic derivatives include dihydroergotamine, dihydroergocristine, bromocriptine, the amides of lysergic acid (such as lysergic acid diethylamide, and lysergic acid hydroxybutamide). Also included are products of the methylation of the indole nitrogen of lysergic acid hydroxybutamide, which is methysergide. "Serotonin agonists" refers to drugs which bind to and stimulate serotonin receptors (e.g., 5HT-1, 5HT-2 etc.).

J. "Migraine," unless otherwise specified, will be understood to include the subset of headaches characterized by unusually severe, unilateral, throbbing, headache pain, usually persisting for 4–72 hours and often including one or more of the following symptoms: nausea, vomiting, sensitivity to light or sound. Migraines are sometimes preceded by an "aura" and visual "scotoma."

K. "Supra-vasoactive syndrome" or SVS shall mean that grouping of adverse reactions and clinical findings generally thought to be due to excessive vasoactivity remote from the intended site of action. SVS comprises one or more of the following symptoms and clinical findings: elevated blood pressure; reduced blood pressure; increased or reduced heart rate; cold extremities; tingling; flushing; feelings of neck or chest pressure, tightness, or heaviness; dizziness; hot or burning sensations; muscle pains; discomfort in the extremities; and frank angina or discomfort of cardiac origin. Thus, "SVS-minimized" shall mean the substantial absence of SVS upon administration of an therapeutically effective amount of an anti-migraine preparation.

L. "Initial migraine relief" shall be understood to be the reduction or abolition of migraine symptoms during the first few hours of an attack and particularly during the first 6 hours.

M. "Relapse headache" variously and interchangeably termed a "rebound," "relapse," "recurrent," "follow on," or "secondary" headache shall mean headaches experienced by migraine patients after having experienced initial relief. A relapse headache may occur during the next 1 to 24 hours.

N. "Unit dosage form" shall mean single drug administration entity. By way of example, a single tablet, capsule, dragee, or trochee (oral unit dosage forms), suppository, or syringe combining both metoclopramide and an NSAID would be a unit dosage form. Administration of the unit dosage form will result in blood levels of the NSAID required to produce a therapeutic effect within about the first hour after dosing and will still be present at least about 8–12 hours after initial dosing, and in particular instances, for as long as about 24 hours after dosing. Blood levels of the metoclopramide establishing effective local gastrointestinal concentration will be present within the first hour and should persist in measurable quantities for at least about 2–6 hours.

A particular type of unit dosage form is an "acid-base storage stable" unit dosage form. "Acid-base storage stable" unit dosage form shall mean a unit dosage form of metoclopramide (a Lewis base, whether in the form of a free base or as an acid salt) and analgesic in which the potency of either active ingredient is not reduced by more than about 15% in 21 days storage at ambient temperature (15–20 degrees C.), or by more than about 5% in 14 days. Acidic analgesic drugs are well known in the art and are exemplified by aspirin. A "non-acidic analgesic" is a compound that has a $pK_a$ of 7 or above when dissolved in water, e.g., celecoxib, $pK_a$=11.1

A "uniform-coated unit dosage form" shall mean a unit dosage form wherein the coating containing metoclopramide remains unchanged within the limits of between 85% and 115% with a relative standard deviation of no more than about 6.4.

O. "Enhanced therapeutic effect" in the context of this invention shall mean that the initial relief of migraine symptoms will occur more quickly and/or more extensively with the combination of two agents compared to the same doses of each component given alone, or that less than standard doses of one or both components can be combined to provide relief of migraine symptoms at least comparable in speed and extent to that achieved with standard doses of either agent.

While the experienced clinician is able to monitor and adjust dosages for each subject relative to the severity of the migraine attack and the presence of side-effects, generally available information on maximum common daily dosages of NSAIDs is useful as a guideline. In particular instances, however, exceeding these "maximum" doses is the therapeutic choice of the medical professional. Maximum daily doses in milligrams is as follows: flurbiprofen 300; ketoprofen 300; naproxen 1500, naproxen sodium 1375; oxaprozin 1800; etodolac 1200; indomethacin 150 to 200; ketorolac 120 mg i.m. and 40 oral; nabumetane 2000; mefenamic acid 1000; and piroxicam 20.

Figure 5A:
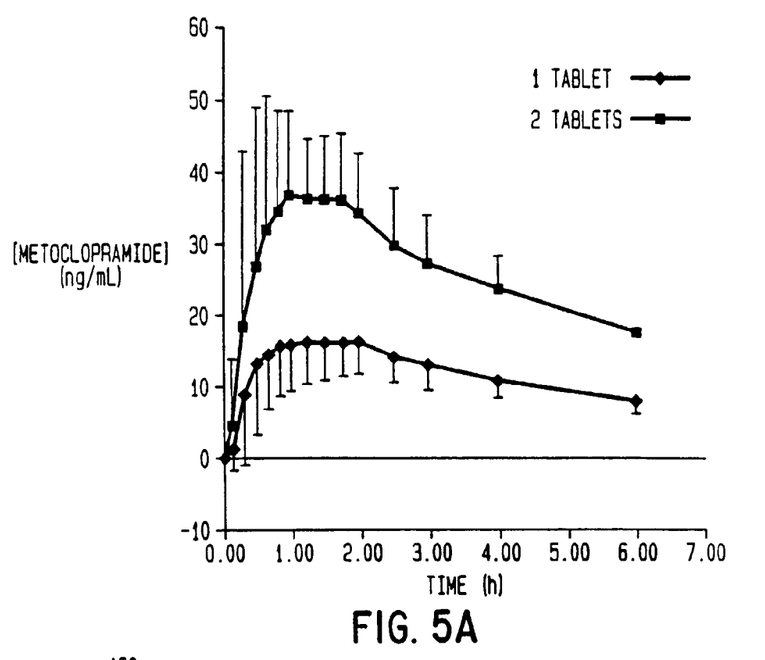
FIG. 5a is a plot of plasma concentrations of metoclopramide upon administration of tablet(s) of the present invention as disclosed in Tablet Example 4.
Figure 5B:
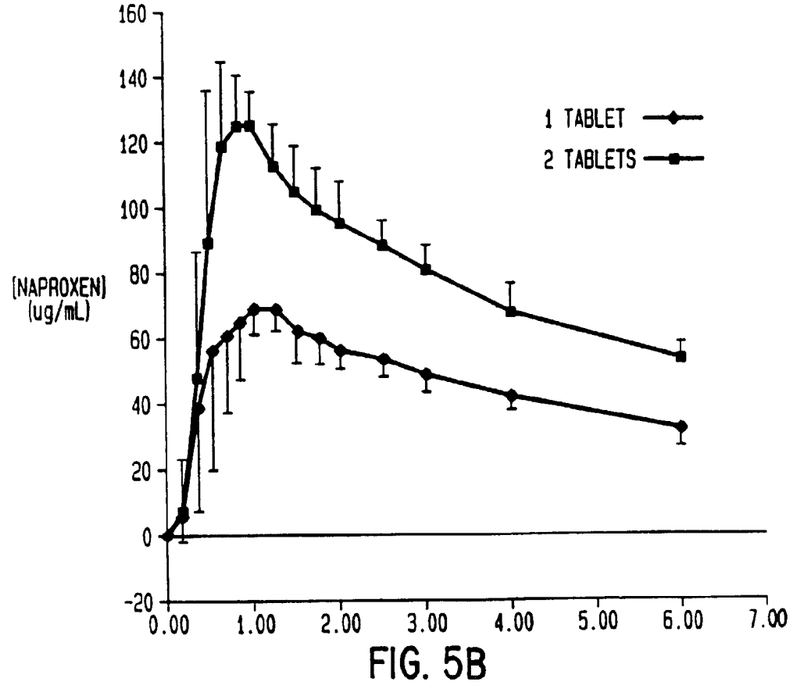
FIG. 5b is a plot of plasma concentrations of naproxen sodium upon administration of tablet(s) of the present invention as disclosed in Tablet Example 4.

P. "Non-spiking" metoclopramide peaks shall mean a plasma concentration of metoclopramide which remains within the limit of variation of its mean value for two or more consecutive time points. As seen in FIG. 5, administration of unit dosage forms of the present invention produced non-spiking peak circulating levels of metoclopramide. The data was obtained from 10 healthy volunteer subjects. On day 1, the subjects were administered one tablet of 500 mg naproxen sodium and 8 mg metoclopramide prepared as described in the Examples section. On day 4, two such tablets were administered. Venous blood samples were collected in $Li^+$ heparin tubes at the times shown. Red and white cells were then separated, and the supernatant deproteinated. The supernatant was then assayed for naproxen and metoclopramide and validated with reference standard by 40 times recrystallization.

Q. "High stability" in reference to sustained metoclopramide plasma levels shall mean less than a 10% deviation (post-$t_{max}$) from the mean over a 15 minute period within 6 hours of administration. Without being bound by any particular theory, it is believed that by combining metoclopramide with an analgesic, and particularly a long-acting NSAID, one can achieve an enhanced therapeutic effect within the first 6 hours after dosing and a lower incidence of relapse headaches for the first 24–48 hours. Furthermore, this effect may be achievable with less than standard doses of one or both of these therapeutic agents. For example, the combination of less than standard doses of metoclopramide and naproxen sodium may result in fewer gastrointestinal complications such as bleeding, ulceration, dyspepsia, heartburn, constipation, and dizziness, drowsiness, and headache due to naproxen sodium and less somnolence, agitation, restlessness, fatigue, and extrapyramidal symptoms including involuntary movements of the limbs, facial grimaces, torticollis, etc. due to the metoclopramide.

EXAMPLES

Example 1

Tablet Formulation #1

Figure 1:
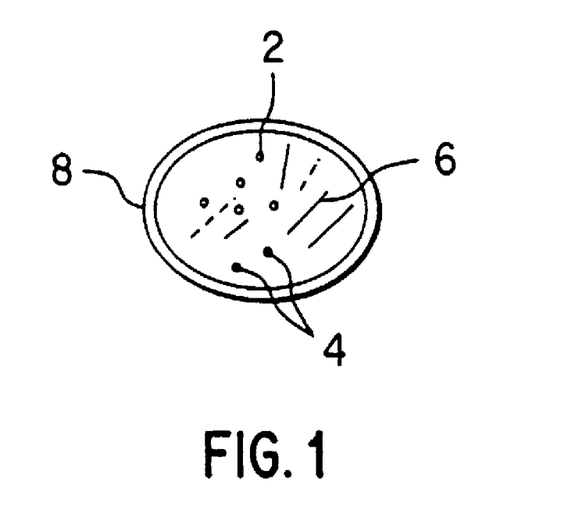
FIG. 1. is a diagrammatic side view of a single layer dosage form of the invention.

A variety of combinations of metoclopramide and analgesic can be made into a single dosage form (e.g., tablet, capsule, suppository) consisting of one or more layers. In this example, a sequentially and rapidly dissolving single layer tablet of metoclopramide, 8 mg, is combined with naproxen sodium, 500 mg. Referring to FIG. 1, this single layer tablet contains naproxen sodium in crystalline form (2) and metoclopramide (4), each uniformly distributed throughout a matrix (6) of pharmaceutically acceptable fillers, excipients, binding agents, disintegrants, and lubricants (collectively, "carrier material"). A pharmaceutically acceptable tablet coating (8) surrounds the active ingredients and carrier materials. Carrier material should be present in an amount of between 50 and 2000 mg, and preferably between 500 and 1,000 mg. Prior to compaction in a tablet, each crystal of naproxen sodium may optionally be coated with excipient. Tablets may include microcrystalline cellulose and magnesium stearate. For example, naproxen sodium may be coated with hydroxypropyl methylcellulose 2910 and polyethylene 8000. A core bulking agent such as lactose may be used in preparations together with a polymer film coating such as Opaspray® b K-1-4210A or Opadry® YS-1-4215 (trademarks of Colorcon, West Point, Pa.). Povidone and talc may also be used as bulking agents for the tablet core.

Tablet stability is compromised in instances in which there is an "acid-base incompatibility" between the metoclopramide and the analgesic. For example, naproxen sodium (the more easily absorbed form of analgesic) is a crystalline solid that is freely soluble in water of neutral pH. Metoclopramide hydrochloride is also freely soluble in water. The basic salt of metoclopramide intimately mixed with acidic naproxen sodium crossreacts in a matter of days causing reduction in tablet potency of about 5% in two weeks and about 20 to 25% or more in three weeks at ambient temperature. Thus, separation between the component active ingredients is advantageous and can be achieved by including either or both active ingredients in barrier coated form. Suitable barrier coating materials for naproxen sodium include OpaDry as applied in combination with water for irrigation and talc. Other materials are shellac, hydroxypropyl methylcellulose phthalate, polyvinyl acetate phthalate, and cellulose acetate phthalate. Thin coatings, on the order of about 25–250 microns, retard the availability of naproxen by no more than about 5 minutes, while substantially extending storage life of the combined formulation.

Example 2

Tablet Formulation #2

Figure 2:
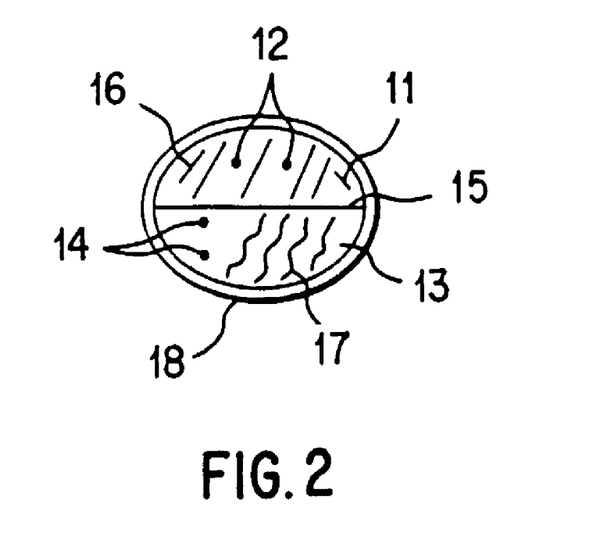
FIG. 2. is a diagrammatic side view of a bilayer dosage form of the invention.

FIG. 2. depicts a sequentially and rapidly dissolving bilayer tablet of metoclopramide, 16 mg, combined with naproxen sodium 500 mg. The tablet consists of a first layer (11) and a second layer (13). The first layer (11) contains naproxen sodium in crystalline form (12) uniformly distributed throughout a matrix (16) of pharmaceutically acceptable fillers, excipients, binding agents, disintegrants, and lubricants (collectively, "first carrier material"). The second layer (13) contains metoclopramide (14) uniformly distributed throughout a matrix (17) of pharmaceutically acceptable fillers, excipients, binding agents, disintegrants, and lubricants (collectively, "second carrier material"). A pharmaceutically acceptable tablet coating (18) surrounds the active ingredients and carrier materials. Dotted line 15 represents the interface between the two layers which are separately molded, poured, compressed or otherwise formed and joined by compression or other tablet forming means. The first carrier material and the second carrier material may be either the same or different.

In one embodiment, the metoclopramide portion may be in effervescent formulation which, upon addition to water, becomes a liquid, and the NSAID, e.g., naproxen, remains in solid form. Tablets may be in the form of a single lozenge, or may form numerous coated beads or granules (with particular reference to sizes within the 4 to 12 sieve range) acting as a slurry in the effervescent solution. A number of tableting techniques are described in *Pharmaceutical Dosage Forms and Drug Delivery Systems*, Ansel et al., Sixth Ed. (Williams & Wilkins, Media Penn., 1995) the teachings of which are incorporated herein by reference.

Example 3

Tablet Formulation #3

A particular example of a tablet in which metoclopramide is in an effervescent matrix separated from analgesic is as follows:

A. Metoclopramide: Metoclopramide in the form of an acid salt is prepared in a particle size of from about 4 to 10 mesh size (4.76 mm to 2.00 mm) formed by moistening blended powders and passing them through a screen or granulator. In this manner, 60 mg of metoclopramide are combined with 250 gm of a mixture of: 200 gm dried dibasic sodium phosphate; 477 gm sodium bicarbonate in dry powder; 252 gm tartaric acid in dry powder; and 162 gm citric acid monohydrate.

B. Naproxen: 500 mg of naproxen sodium are compacted as granules with: povidone k-29/32 (23.6 mg); microcrystalline cellulose, NF (105.9 mg); croscarmellose sodium, NF, (13.5 mg); talc (27 mg); and magnesium stearate (5 mg).

C. The metoclopramide granules and the naproxen are combined into a two-layer tablet as described in Example 2.

Example 4

Tablet Formulation #4

Figure 3:
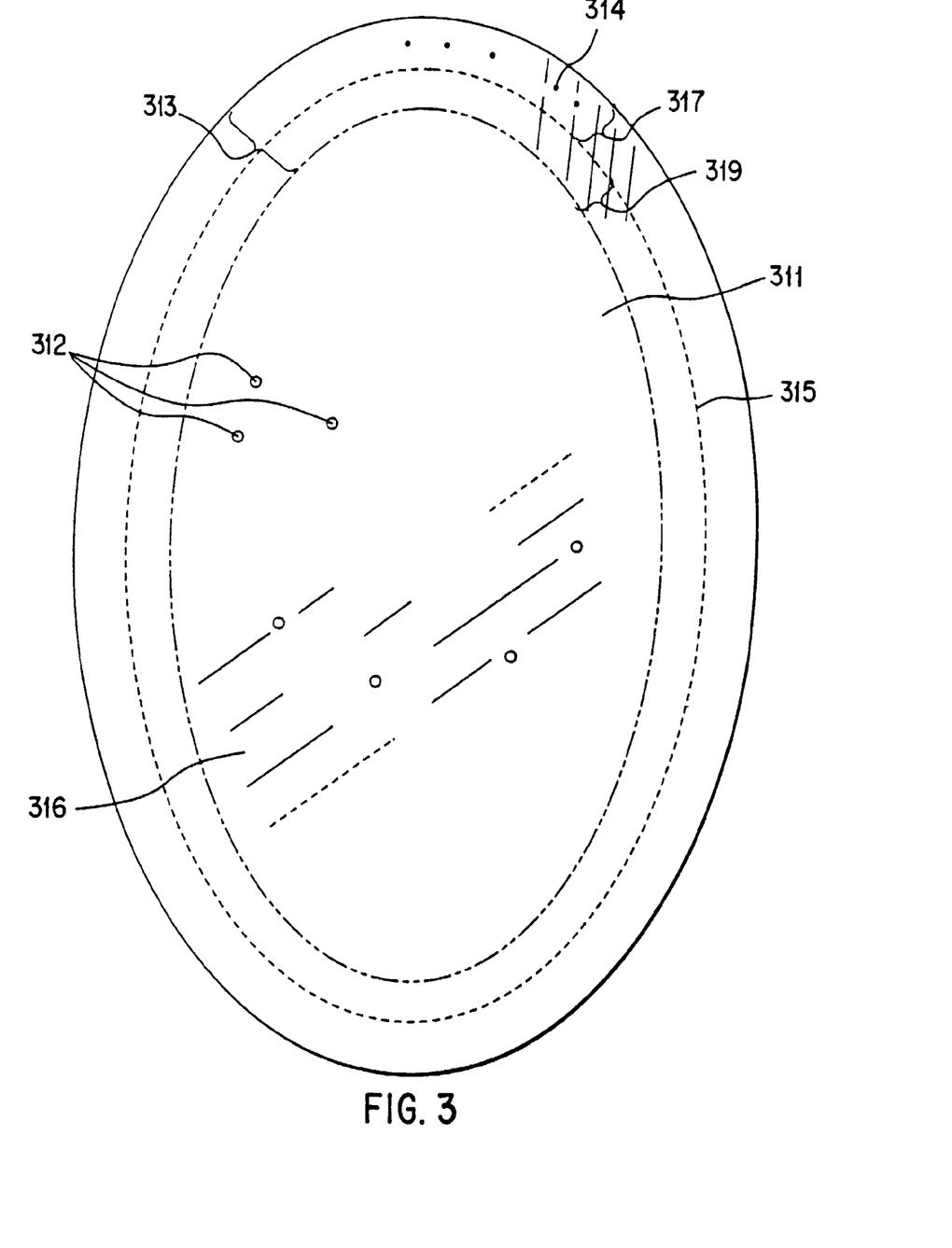
FIG. 3. is a diagrammatic side view of another bilayer dosage form of the invention.

FIG. 3. depicts another example of a sequentially and rapidly dissolving bilayer tablet in which metoclopramide hydrochloride (8 mg) is combined with naproxen sodium (500 mg). Referring to the figure, the bilayer tablet consists of a first layer (311) and a second layer (313) having an exterior portion (317) and an interior portion (319). The first layer (311) contains naproxen sodium granules in crystalline form (312) uniformly distributed throughout a matrix (316) of pharmaceutically acceptable fillers, excipients, binding agents, disintegrants, and lubricants (collectively, "first carrier material"), to form a core. The second layer (313) contains metoclopramide hydrochloride in crystalline form 314) uniformly distributed throughout the exterior portion of layer (313), wherein (317) comprises a matrix of pharmaceutically acceptable tablet coating. A tablet coating (317) surrounds both the second layer as well as the layer of naproxen and carrier material (311). Dotted line (315) represents the interface between the exterior portion (313) and the interior portion (319). This interface may comprise titanium dioxide, carnauba wax, shellac, cellulose acetate phthalate or the like. Interior portion (319) may comprise about 2 to 3% of the coating material of (313) and separates the naproxen layer or core from the metoclopramide. As depicted diagrammatically in FIG. 3, the portion of the coating layer below line (315) is comprised of the same coating material as matrix (317). This architecture separates the acidic naproxen from the basic form of metoclopramide.

The naproxen-containing portion of tablets may be separately molded, poured, compressed or otherwise formed and joined by compression or other tablet forming means. It is then spray coated with a material absent metoclopramide, e.g., HPMC, triethyl citrate, and TiO2 applied in an aqueous spray. Coatings of 1 to 10%, and preferably 2 to 3%, of the total coating weight are useful. Later, a second spray coating which includes metoclopramide hydrochloride is applied and serves to further segregate metoclopramide from naproxen. A preferred second coating comprises: HPMC (35 to 55%, preferably 42 to 47% and most preferably about 45%); titanium dioxide (3 to 8%, preferably 4 to 6% and most preferably about 5%); triethylcitrate (0.05 to 0.3%, preferably 0.07 to 0.2% and most preferably about 0.1%); talc (17% to 35%, preferably 21 to 27% and most preferably about 24%; and metoclopramide (10 to 40%, preferably 20 to 30% and most preferably about 26%). The metoclopramide hydrochloride may be suspended in coating solution that is applied to a core consisting of about 100–1000 mg of naproxen sodium, and preferably about 500 mg.

Preparation of a tablet of FIG. 3 requires particular attention to the application of metoclopramide in such a manner as to maintain acceptable tablet dosage uniformity ("uniform-coated unit dosage form"). Coating should be uniform to between 85% and 115% of the intended dosage with a relative standard deviation of 6.4 or less. With pancoating methodology, it is important to control pan speed, movement of tablets across the tablet bed, spray temperature and spray coverage relative to the entire pan. Tablets sticking to each other or to the pan during coating will reduce uniformity. Thus, it is advantageous to apply a coating material that does not readily stick to the pan, and to agitate tablets ("agitating rotation") during coating such that tablets do not stick to each other. Employing a coating pan with baffles offers agitating rotation of the tablets being coated. A coating that does not cause tablets to stick to each other during agitating rotating in a coating pan is termed an "adhesion reduced" coating. An example of an additive that may be used to produce an adhesion reduced coating is talc (at least 18%, preferably at least 20% and most preferably at least 24% of the dry weight of the metoclopramide-containing outer portion).

Figure 6:
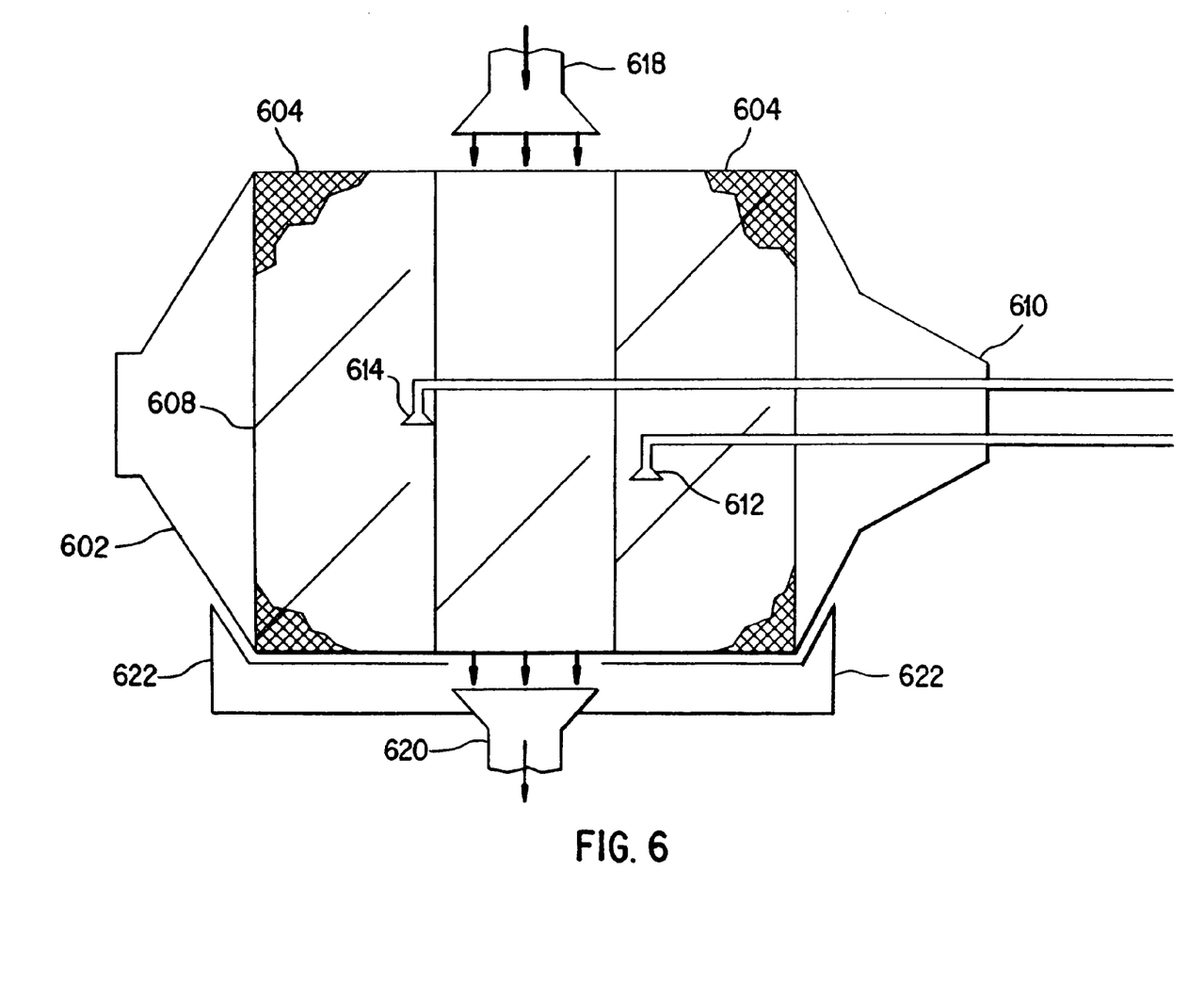
FIG. 6 is a diagrammatic cross section side view of a tablet coating pan with baffles and spray nozzles.

FIG. 6 depicts an apparatus for coating tablets. A rotating coating pan (602) is partially filled with tablet cores to be coated. In the embodiment shown, screen panels (604) facilitate air circulation, and baffles (608) placed on the coating pan walls agitate tablet cores during rotation. Spray nozzles (612) and (614)) leading from a spray mixture reservoir, and pump means spray coating through an inlet (610) over tablet cores. An air source (618) introduces drying air into the coating pan from a heating and pumping source (not shown). Air exits through a vacuum outlet (620) as well as through screen panels (604). The coating pan is agitated by a rotating means (622).

A preferred method of making tablets is to coat NSAID cores, particularly naproxen cores, with an atomized coating mixture while the cores are in a rotating pan. Although not limited to any particular apparatus, suitable devices are the Driacoater/Vario 500/600 (Driam USA, Spartanburg, Pa.) and spray guns such as the 460 Bink spray gun (Binks Manufacturing Company, Franklin Park Ill.)). Using two spray guns about 10 to 12 inches apart and 4 to 8 inches above the tablet bed should produce a suitable coating when pans are rotated at a speed of 14 to 16 rpm. It is particularly important to maintain tablet movement in the pan to avoid tablet sticking and enhance coating uniformity.

Example 5

Tablet Formulation #5 (Metoclopramide Film Coated Tablet)

This acid-base storage stable uniform-coated unit dosage form has metoclopramide as a film in the outermost portion of the tablet and separated from the naproxen sodium. The final tablet formulation by weight is as follows:

| A. | metoclopramide hydrochloride | 8 mg |
| --- | --- | --- |
| | (i) metoclopramide-containing coating (in percentage of total metoclopramide containing coating dry weight) | |
| | hydroxypropyl methylcellulose | 45% ± 5% |
| | titanium dioxide | 5% ± 2% |
| | triethyl citrate | 0.1% ± 0.5% |
| | metoclopramide | 26% ± 1% |
| | talc | 24% ± 1% |
| | (ii) metoclopramide free coating (in percentage of total tablet dry weight) | |
| | hydroxypropyl methylcellulose | 9% |
| | titanium dioxide | 1% |
| | triethyl citrate | 2% |
| B. | naproxen core | |
| | naproxen sodium | 500 mg |
| | povidone k-29/32 | 23.6 mg |
| | microcrystalline cellulose, NF, | 105.9 mg |
| | croscarmellose sodium, NF | 13.5 |
| | talc | 27 mg |
| | magnesium stearate | 5 mg |

To prepare a two layer tablet as in FIG. 3., particular attention is paid to the application of the film coating. Naproxen cores are placed in the coating pan with baffles in place and with a rotation speed of about 14–16 rpm. From two spray guns mounted about 4 to 8 inches apart and 10 to 12 inches above the tablet bed, atomized metoclopramide-free coating mixture is sprayed over the rotating pan until the cores increase from about 2% to about 3% in weight. Continuous drying is performed by air input at about 65° C.±5°, and with an exhaust temperature of 45° C.±5°. Spraying pressure when the atomizer is set at 2.0–4.0 yields a spray particle size of about 10 μm to about 200 μm and averaging about 50 μm.

After the initial coating step, tablets are again spray coated in the rotating baffled pan, but now with a metoclopramide-containing coating material until the tablet weight increases from about 8 to about 10% over the weight of the naproxen core. For example, sufficient spraying may be performed to apply 8 mg of metoclopramide to each tablet.

After spraying is complete, tablets are examined for uniformity in keeping with the requirement of a "uniform-coated unit dosage form." Testing the content of metoclopramide HCl should confirm that the metoclopramide in the coating of each tablet is between 85% and 115% of the calculated dosage with a standard deviation of no more than 6.4.

Example 6

Examination of Tablet Dissolution Time

Figure 4:
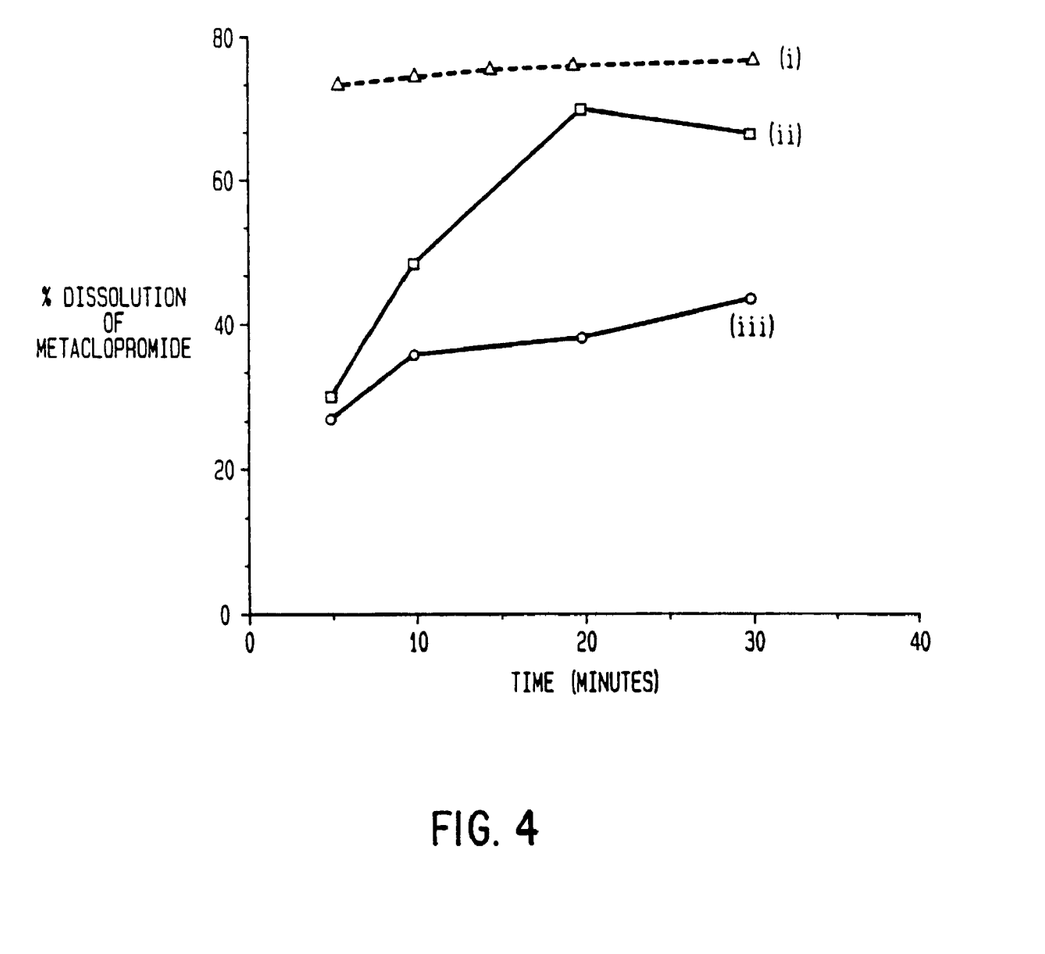
FIG. 4. is a comparative dissolution plot of the metoclopramide presented in a tablet coating layer and presented in a compressed tablet layer.

A comparison of dissolution times was made between unit dosage forms. Dissolution was determined by USP apparatus #2 for which, 70–80% represents essentially total dissolution (unless stirrer speeds are markedly increased). Data is presented in FIG. 4 for:

(i) naproxen sodium and metoclopramide HCl, each in a separate layer but with the metoclopramide in a coating film (see Example 5)
(ii) naproxen sodium and metoclopramide HCl in a single matrix not acid-base stable, but newly made; and
(iii) naproxen sodium and metoclopramide HCl in a single matrix not acid-base stable, after 14 days storage at ambient temperature 15°–20° C.).

Essentially complete solubilization of metoclopramide from the oral dosage form was observed within about 5 minutes (using 0.01 M to 0.1 M HCl) for the tablet of Example 4.

Example 7

First Treatment Example

An adult female migraineur complains of a migraine attack with typical symptoms: headache, nausea and sensitivity to light and sound. She is administered a single oral (single layer) tablet containing metoclopramide (8 mg) and naproxen sodium (250 mg). Her symptoms start to diminish within one hour and, by three hours, she is completely symptom free. No relapse over the next 48 hours is reported.

Example 8

Second Treatment Example

An adult female migraineur complains of a migraine attack with typical symptoms: migraine headache, nausea and sensitivity to light and sound. She is administered a single oral (bilayer) tablet containing metoclopramide (16 mg) and naproxen sodium (500 mg). Her symptoms start to diminish within one hour. By three hours, she is completely symptom free and has no relapse over the next 48 hours.

Example 9

Third Treatment Example

The same symptoms as in the patients of Example 7 and 8 are presented by a male, 25 years of age. Upon oral administration of a single layer tablet containing 16 mg of metoclopramide and 1000 mg naproxen sodium the same result is obtained.

The metoclopramide and NSAID combined compositions of this and the previous examples may conveniently be prepared at several unit dosage form strengths, e.g., 8 mg metoclopramide/500 mg naproxen sodium; 16 mg metoclopramide/500 mg naproxen sodium; 8 mg metoclopramide/250 mg naproxen sodium; 16 mg metoclopramide/250 mg naproxen sodium.

Example 10

Fourth Treatment Example

An adult female migraineur complains of a migraine attack consisting of typical symptoms: headache, nausea and sensitivity to light and sound. She is administered a tablet prepared according to Example 5 containing metoclopramide (8 mg) and naproxen sodium (500 mg). The naproxen moves from the stomach into the duodenum within 5 minutes of dosing. Her symptoms start to diminish within one hour and by three hours she is completely symptom free. No relapse occurs over the next 48 hours.

Example 11

Clinical Study of Pharmacokinetics

The absorption and elimination kinetics of a single dose of a metoclopramide/naproxen preparation, "MT 100," (16 mg metoclopramide hydrochloride and 500 mg naproxen sodium) was compared to naproxen sodium alone (500 mg); metoclopramide hydrochloride alone (16 mg); and two tables of MT 100 in a randomized, four-period, cross-over Phase I study. Twenty-four healthy volunteers (14 females and 10 males), aged 20–55 years, received each of the four treatments. Blood samples for determination of plasma concentrations of naproxen and metoclopramide were collected at the following times: 0, 10, 20, 30, 40, 50, 60, 75 and 90 minutes, and 2, 4, 6, 12, 24, 48 and 72 hours post dosing. Standard pharmacokinetic parameters were calculated, including maximum plasma concentrations over the entire sampling phase (Cmax), time to attain maximal plasma concentrations (Tmax), and area under the plasma concentration-time curve (AUCI-time 0 to infinity).

For metoclopramide, dose proportionality was shown in comparing the kinetics (AUCI and Cmax) of a single dose of MT 100 with 2 tablets of MT 100 (see Table 1 below). Time to maximal concentration was unchanged between doses. Cmax and AUCI were slightly less than dose proportional for naproxen concentrations. This finding is likely due to increased clearance at the higher dose of MT 100, as naproxen is known to be highly protein bound and renal elimination can increase once binding sites have been saturated.

TABLE 1

Pharmacokinetic of a Single Dose of MT 100 and 2 Tablets of MT 100

| PK Parameter | MT 100 (1 tab) | | MT 100 (2 tabs) | |
|---|---|---|---|---|
| | MC[1] | NAP[2] | MC[1] | NAP[2] |
| AUCI [μg*hr/mL] | 643 | 1292 | 1278 | 1934 |
| Cmax [μg/mL] | 58.4 | 96.9 | 116.1 | 151.6 |
| Tmax [hr] | 1.32 | 0.72 | 1.36 | 0.80 |

[1]Metoclopramide
[2]Naproxen

As a result of its gastric pro-kinetic effects, it was expected that metoclopramide might speed the absorption of naproxen when the two were delivered together in the coordinated-release MT 100 dosage form. As shown in Table 2, this was demonstrated based on a comparison of plasma naproxen levels for a single MT 100 tablet vs. those for the tablet containing naproxen sodium alone. The presence of metoclopramide resulted in an earlier Tmax (by approximately 30 minutes) and a slightly higher maximal plasma naproxen concentration.

TABLE 2

Pharmacokinetics of Naproxen in MT 100 Versus Naproxen Sodium

| PK Parameter | MT 100 | Naproxen Sodium |
|---|---|---|
| Cmax [μg/mL] | 96.9 | 84.4 |
| Tmax [hr] | 0.72 | 1.20 |

The pharmacokinetics of MT 100 showed an increased Cmax for the metoclopramide and naproxen in the female subjects, with the Tmax remaining relatively constant (Table 3).

TABLE 3

Pharmacokinetics of MT 100 by Gender

| | NAP in MT 100 (1 tab) | | MC in MT 100 (1 tab) | |
|---|---|---|---|---|
| PK Parameter | Male | Female | Male | Female |
| Cmax [μg/mL] | 88.8 | 102.7 | 39.4 | 71.9 |
| Tmax [hr] | 0.75 | 0.70 | 1.20 | 1.40 |

In general, all doses of MT 100, naproxen and metoclopramide were well tolerated in this study.

Example 12

Phase III Clinical Study of Efficacy

One thousand sixty-four migraine patients participated in a phase III, randomized, single-dose, double-blind, parallel group study designed to compare the safety and efficacy of MT 100 (16 mg metoclopramide hydrochloride and 500 mg naproxen sodium) versus its individual components of naproxen sodium (NAP) and metoclopramide hydrochloride (MC). The randomization schedule was imbalanced by design and resulted in 422, 428, and 214 patients being treated with MT 100, NAP, and MC, respectively. The MC group functioned as the placebo group for comparative purposes since MC was demonstrated in an earlier phase II study to be without significant effect on pain variables.

Several measures were used to assess response, including "sustained response," defined as a reduction of moderate or severe pain to no pain or only mild pain at 2 hours without a return to either moderate or severe pain or the use of rescue medicine over the next 22 hours. "Complete response," was also calculated and is defined in the same way as sustained response with the exception that it ignores the use of rescue medicine. Other measures included assessments of pain intensity differences (PID) and sum of pain intensity differences (SPID) at each time point, total pain relief (TOTPAR) at each time point, sustained pain free status, response (reduction of moderate or severe pain to no or mild pain) at each time point, use of rescue medicines, nausea relief and time to nausea relief, as well as assessments of other migraine symptoms at each time point. Relapse, defined as the recurrence of headache pain to moderate or severe levels in patients who had attained either no or mild pain status at 2 hours, was also recorded.

MT 100 was superior to MC (placebo-equivalent) with respect to pain relief (PID, SPID, TOTPAR) beginning at one hour after dosing and continuing throughout the remainder of the 24 hour follow-up period. MT 100 was also superior to MC as measured by the sustained response rate, complete response rate and the sustained pain free rate. MT 100 was also superior to MC with respect to the 2 hour pain relief rate, pain free rate and for most other efficacy variables except those associated with nausea relief.

Compared to NAP, MT 100 was superior with respect to pain measures. Sustained response and complete response were higher for MT 100 than for NAP. The long lasting benefit of MT 100 over NAP was confirmed by the superiority of the MT 100 24 hour SPID score and 24 hour TOTPAR score. Consistent with its longer duration of action, there were significantly fewer patients requiring rescue medicine, and the time to rescue was significantly longer in the MT 100 group. Fifty percent fewer 2 hour responders with MT 100 had a return to either moderate or severe pain score within 22 hours compared to NAP. Additionally, greater nausea relief was seen at one hour with MT 100 vs. NAP as evidenced by higher nausea relief scores.

Adverse events were uncommon and there appear to be no differences in the incidence of any adverse events between groups. Only somnolence and diarrhea were reported by more than 2% of patients in any treatment group. In general, MT 100 was extremely well tolerated.

What is claimed is:
1. A pharmaceutical composition in unit dosage form suitable for oral administration to a human for the treatment of migraine headache, wherein said unit dosage form is a tablet or capsule, comprising: metoclopramide and an acidic NSAID having a $pK_a$ below 7 when dissolved in water, present in an amount such that the combination is effective in reducing or eliminating pain associated with said migraine headache and wherein said dosage form is acid-base storage stabilized due to:
a) a barrier coating separating said metoclopramide from said acidic NSAID; or
b) said acidic NSAID and said metoclopramide being segregated into separate layers of a multilayer tablet in a way that prevents said metoclopramide and said acidic NSAID from contacting one another.

2. The pharmaceutical composition of claim 1, wherein said unit dosage form is substantially free of any 5 HT agonist vasoactive agent and wherein said NSAID has a half-life of 8–14 hours.

3. The pharmaceutical composition of claim 1, wherein said unit dosage form is coordinated.

4. The pharmaceutical composition of claim 1, wherein said acidic NSAID is long acting.

5. A pharmaceutical composition in unit dosage form suitable for oral administration to a human for the treatment of migraine headache, wherein said unit dosage form is a tablet or capsule, comprising: metoclopramide and an acidic NSAID, present in an amount such that the combination is effective in reducing or eliminating pain associated with said migraine headache and wherein said dosage form is acid-base storage stabilized as a result of:
a) a barrier coating separating said metoclopramide from said acidic NSAID; or
b) said acidic NSALD and said metoclopramide being segregated into separate layers of a multilayer tablet in a way that prevents said metoclopramide and said acidic NSAID from contacting one another;
and wherein said acidic NSAID is selected from the group consisting of: ibuprofen; flurbiprofen; ketoprofen; naproxen; oxaprozin; etodolac; indomethacin; ketorolac; piroxicam; meloxicam; and a pharmaceutically acceptable salt thereof.

6. The pharmaceutical composition of claim 5, wherein said acidic NSAID is ibuprofen or a pharmaceutically acceptable salt thereof.

7. The pharmaceutical composition of claim 5, wherein said acidic NSAID is flurbiprofen or a pharmaceutically acceptable salt thereof.

8. The pharmaceutical composition of claim 5, wherein said acidic NSAID is ketoprofen or a pharmaceutically acceptable salt thereof.

9. The pharmaceutical composition of claim 5, wherein said acidic NSAID is oxaprozin or a pharmaceutically acceptable salt thereof.

10. The pharmaceutical composition of claim 5, wherein said acidic NSAID is etodolac or a pharmaceutically acceptable salt thereof.

11. The pharmaceutical composition of claim 5, wherein said acidic NSAID is indomethacin or a pharmaceutically acceptable salt thereof.

12. The pharmaceutical composition of claim 5, wherein said acidic NSAID is ketorolac or a pharmaceutically acceptable salt thereof.

13. The pharmaceutical composition of claim 5, wherein said acidic NSAID is piroxicam or a pharmaceutically acceptable salt thereof.

14. The pharmaceutical composition of claim 5, wherein said acidic NSAID is meloxicam or a pharmaceutically acceptable salt thereof.

15. The pharmaceutical composition of claim 5, wherein said acidic NSAID is naproxen or a pharmaceutically acceptable salt thereof, said naproxen being present in an amount of 50–1500 mg.

16. The pharmaceutical composition on claim 15, wherein said naproxen is present in an amount of 200–600 mg.

17. The pharmaceutical composition of claim 5, wherein said acidic NSAID or pharmaceutically acceptable salt thereof is naproxen sodium.

18. The pharmaceutical composition of claim 17, wherein said naproxen sodium is present in an amount of 275–550 mg.

19. The pharmaceutical composition of any one of claims 5–12, 13, 14–18, wherein said unit dosage form is substantially free of any 5 HT agonist vasoactive agent.

20. The pharmaceutical composition of any one of claims 5–12, 13, 14–18, wherein said unit dosage form is coordinated.

21. A method of treating a human for migraine headache comprising:
administering to said human a dosage form according to any one of claims 1, 2, 3, 4, 5–12, 13, 14–18 in an amount effective to reduce or eliminate one or more symptoms associated with said migraine headache.

22. The method of claim 21, where said dosage form is substantially free of any 5 HT agonist vasoactive agent.

23. The method of claim 21, where said dosage form is coordinated.

* * * * *